US006518416B1

(12) United States Patent
Danenberg

(10) Patent No.: US 6,518,416 B1
(45) Date of Patent: Feb. 11, 2003

(54) **METHOD OF DETERMINING A CHEMOTHERAPEUTIC REGIMEN BASED ON *ERCC1* EXPRESSION**

(75) Inventor: Kathleen D. Danenberg, Altadena, CA (US)

(73) Assignee: Response Genetics, Inc., New York, NY (US)

( * ) Notice: Subject to any disclaimer, the term of this patent is extended or adjusted under 35 U.S.C. 154(b) by 0 days.

(21) Appl. No.: 09/796,491

(22) Filed: Mar. 2, 2001

Related U.S. Application Data

(60) Provisional application No. 60/250,121, filed on Dec. 1, 2000, and provisional application No. 60/250,470, filed on Dec. 4, 2000.

(51) Int. Cl.[7] .................. C07H 21/04; C12N 15/11; C12P 19/34
(52) U.S. Cl. ................. 536/24.33; 536/24.3; 536/23.1; 435/91.1; 435/91.2; 435/810
(58) Field of Search .................. 536/24.33, 24.3, 536/23.1

(56) References Cited

U.S. PATENT DOCUMENTS

| | | | |
|---|---|---|---|
| 5,705,336 A | 1/1998 | Reed et al. ..................... | 435/6 |
| 5,994,076 A | 11/1999 | Chenchik et al. ............... | 435/6 |
| 6,204,375 B1 | 3/2001 | Lader ........................ | 536/25.4 |
| 6,207,408 B1 | 3/2001 | Essenfeld et al. .......... | 435/40.5 |
| 6,248,535 B1 | 6/2001 | Danenberg et al. ............ | 435/6 |

OTHER PUBLICATIONS

Stratagene Catalog 1988.*
GenBank Accession No. M13194.*
Iqbal S, Lenz HJ, "Determinants of prognosis and response to therapy in colorectal cancer,"Curr Oncol Rep. Mar. 2001;3(2):102–8.
Gilmore PM, et al., "The Development and Optimisation of a Quantitative RT–PCR Technique from Formalin–Fixed and Paraffin–Embedded (FFPE) Tissues, Using the Thymidylate Synthase (TS) Gene As a Target," American Society of Clinical Oncology: 17: Abstract 2159, 1998.
Salonga D. Danenberg KD, Johnson M, Metzger R, Groshen S, Tsao–Wei DD, Lenz HJ, Leichman CG, Leichman L, Diasio RB, Danenberg PV, "Colorectal tumors responding to 5–fluorouracil have low gene expression levels of dihydropyrimidine dehydrogenase, thymidylate synthase, and thymidine phosphorylase," Clin Cancer Res. Apr. 2000;6(4):1322–7.
Specht K, Richter T, Muller U, Walch A, Werner M, Hofler H, "Quantitative gene expression analysis in microdissected archival formalin–fixed and paraffin–embedded tumor tissue," Am J Pathol. Feb. 2001;158(2):419–2.
Gibson, UE, "A novel method for real timequantitative RT–PCR," Genome Res 6: 995–1001, 1996.
Heid, CA, "Real Time quantitative PCR," Genome Res 6: 986–994, 1996.

Schena, Mark et al. "Quantitative Monitoring of Gene Expression Patterns With a Complementary DNA Microarray", Science (1995) vol. 270:467–470.
Zhao, Nanding et al., "High–Density cDNA Filter Analysis: A Novel Approach for Large–Scale, Quantitative Analysis of Gene Expression", Gene (1995) vol. 156: 207–213.
Dabholkar M, Thornton K, Vionnet J, Bostick–Bruton F, Yu JJ, Reed E, "Increased mRNA levels of xeroderma pigmentosum complementation group B (XPB) and Cockayne's syndrome complementation group B (CSB) without increased mRNA levels of multidrug–resistance gene (MDR1) or metallothionein–II (MT–II) in platinum–resistant human ovarian cancer tissues." Biochem Pharmacol. Dec. 1, 2000;60(11):1611–9.
Damia G, Guidi G, D'Incalci M, "Expression of genes involved in nucleotides excision repair and sensitivity to cisplatin and melphalan in human cancer cell lines," Eur J Cancer, Oct. 1998;34(11):1783–8.
Codegoni AM, Broggini M, Pitelli MR, Pantarotto M, Torri V, Mangioni C, D'Incalci M, "Expression of genes of potential importance in the response to chemotherapy and DNA repair in patients with ovarian cancer," Gynecol Oncol. Apr. 1997; 65(1):130–7.
Zhao R, Rabo YB, Egyhazi S, Andersson A, Edgren MR, Linder S, Hansson J., "Apoptosis and c–jun induction by cisplatin in a human melanoma cell line and a drug–resistant daughter cell line," Anticancer Drug, Oct. 1995;6(5):657–68.
Dabholkar M, Bostick–Bruton F, Weber C, Egwuagu C, Bohr VA, Reed E., "Expression of excision repair genes in non–malignant bone marrow from cancer patients," Mutat Res. Jan. 1993;293(2):151–60.
Dabholkar M, Bostick–Bruton F, Weber C, Bohr VA, Egwuagu C, Reed E., "ERCC1 and ERCC2 expression in malignant tissues from ovarian cancer patients," J Natl Cancer Inst. Oct. 7, 1992;84(19):1512–7.

(List continued on next page.)

*Primary Examiner*—Kenneth R. Horlick
*Assistant Examiner*—Alexander H. Spiegler
(74) *Attorney, Agent, or Firm*—Kenyon & Kenyon

(57) ABSTRACT

The present invention relates to prognostic methods which are useful in medicine, particularly cancer chemotherapy. The object of the invention to provide a method for assessing ERCC1 expression levels in fixed or fixed and paraffin embedded tissues and prognosticate the probable resistance of a patient's tumor to treatment with platinum-based therapies by examination of the amount of ERCC1 mRNA in a patient's tumor cells and comparing it to a predetermined threshold expression level. More specifically, the invention provides to oligonucleotide primer pair ERCC1 and methods comprising their use for detecting levels of ERCC1 mRNA.

3 Claims, 1 Drawing Sheet

OTHER PUBLICATIONS

Metzger R, et al., "ERCC1 mRNA Levels Complement Thymidylate Synthase mRNA Levels in predicting response and survival for gastric cancer patients receiving combination cisplatin and fluorouracil chemotherapy," J Clin Oncol 16: 309–316, 1998.

Taverna P, Hansson J, Scanlon KJ, Hill BT, "Gene expression in X–irradiated human tumour cell lines expressing cisplatin resistance and altered DNA repair capacity," Carcinogenesis. Sep. 1994;15(9):2053–6.

Dabholkar M, Vionnet J, Bostick–Bruton F, Yu JJ, Reed E. Messenger RNA levels of XPAC and ERCC1 in ovarian cancer tissue correlate with response to platinum–based chemotherapy. J Clin Invest. Aug. 1994;94(2):703–8.

Li Q, Yu JJ, Mu C, Yunmbam MK, Slavsky D, Cross CL, Bostick–Bruton F, Reed E. Association between the level of ERCC–1 expression and the repair of cisplatin–induced DNA damage in human ovarian cancer cells. Anticancer Res. Mar.–Apr. 2000;20(2A):645–52.

Johnston et al., TS Expression from Formalin Fixed Paraffin Embedded (FFPE) tissues using Quantitative RT–PCR correlates with frozen tissue data and predicts for response to 5–FU in metastatic colorectal cancers. American Society of Clinical Oncology: Astract 2383, 1999.

Miyauchi, et al., "Further study of Hepatitis C virus RNA detection in formalin –fixed, paraffin –embedded liver tissues by ligation –dependent polymerase chain reaction" Pathology International 1998:48: 428–432.

G. Stanta, et al., *RNA Quantitative Analysis from Fixed and Paraffin–Embedded Tissues*, Methods in Molecular Biology (1998) vol. 86, pp. 113–119.

G. Stanta, et al., *RNA Extraction from Formalin–Fixed and Paraffin–embedded Tissues*, Methods in Molecular Biology (1998) vol. 86, pp. 23–26.

* cited by examiner

METHOD OF DETERMINING A CHEMOTHERAPEUTIC REGIMEN BASED ON ERCC1 EXPRESSION

RELATED APPLICATIONS

This application claims priority to the following applications: No. 60/250,121 filed Dec. 1, 2000 and No. 60/250,470 filed Dec. 4, 2000.

FIELD OF THE INVENTION

The present invention relates to prognostic methods which are useful in medicine, particularly cancer chemotherapy. More particularly, the invention relates to assessment of tumor cell gene expression in a patient. The resistance of tumor cells to chemotherapeutic agents that target DNA, especially agents that damage DNA in the manner of platinating agents is assayed by examining the mRNA expressed from genes involved in DNA repair in humans.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes. These generally are referred to as antimetabolite drugs. Other classes of chemotherapeutic drugs inflict damage on cellular DNA. Drugs of these classes generally are referred to as genotoxic. Susceptibility of an individual neoplasm to a desired chemotherapeutic drug or combination of drugs often, however, can be accurately assessed only after a trial period of treatment. The time invested in an unsuccessful trial period poses a significant risk in the clinical management of aggressive malignancies.

The repair of damage to cellular DNA is an important biological process carried out by a cell's enzymatic DNA repair machinery. Unrepaired lesions in a cell's genome can impede DNA replication, impair the replication fidelity of newly synthesized DNA and/or hinder the expression of genes needed for cell survival. Thus, genotoxic drugs generally are considered more toxic to actively dividing cells that engage in DNA synthesis than to quiescent, nondividing cells. Normal cells of many body tissues, however, are quiescent and commit infrequently to re-enter the cell cycle and divide. Greater time between rounds of cell division generally is afforded for the repair of DNA damage in normal cells inflected by chemotherapeutic genotoxins. As a result, some selectivity is achieved for the killing of cancer cells. Many treatment regimes reflect attempts to improve selectivity for cancer cells by coadministering chemotherapeutic drugs belonging to two or more of these general classes.

Because effective chemotherapy in solid tumors usually requires a combination of agents, the identification and quantification of determinants of resistance or sensitivity to each single drug has become an important tool to design individual combination chemotherapy.

Two widely used genotoxic anticancer drugs that have been shown to damage cellular DNA are cisplatin (DDP) and carboplatin. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin currently is preferred for the management of testicular carcinoma, and in many instances produces a lasting remission. (Loehrer et al., 1984, 100 Ann. Int. Med. 704). Cisplatin (DDP) disrupts DNA structure through formation of intrastrand adducts. Resistance to platinum agents such as DDP has been attributed to enhanced tolerance to platinum adducts, decreased drug accumulation, or enhanced DNA repair. Although resistance to DDP is multifactoral, alterations in DNA repair mechanisms probably play a significant role. Excision repair of bulky DNA adducts, such as those formed by platinum agents, appears to be mediated by genes involved in DNA damage recognition and excision. Cleaver et al., Carcinogenesis 11:875–882 (1990); Hoeijmakers et al., Cancer Cells 2:311–320 (1990); Shivji et al., Cell 69:367–374 (1992). Indeed, cells carrying a genetic defect in one or more elements of the enzymatic DNA repair machinery are extremely sensitive to cisplatin. Fraval et al. (1978), 51 Mutat. Res. 121, Beck and Brubaker (1973), 116 J. Bacteriol 1247.

The excision repair cross-complementing (ERCC1) gene is essential in the repair of DNA adducts. The human ERCC1 gene has been cloned. Westerveld et al., Nature (London) 310:425–428 (1984); Tanaka et al., Nature 348:73–76 (1990). Several studies using mutant human and hamster cell lines that are defective in this gene and studies in human tumor tissues indicate that the product encoded by ERCC1 is involved in the excision repair of platinum-DNA adducts. Dabholkar et al., J. Natl. Cancer Inst. 84:1512–1517 (1992); Dijt et al., Cancer Res. 48:6058–6062 (1988); Hansson et al., Nucleic Acids Res. 18: 35–40 (1990).

When transfected into DNA-repair deficient CHO cells, ERCC1 confers cellular resistance to cisplatin along with the ability to repair platinum-DNA adducts. Hansson et al., Nucleic Acids Res. 18: 35–40 (1990). Currently accepted models of excision repair suggest that the damage recognition/excision step is rate-limiting to the excision repair process.

The relative levels of expression of excision repair genes such as ERCC1 in malignant cells from cancer patients receiving platinum-based therapy has been examined. Dabholkar et al., J. Natl. Cancer Inst. 84:1512–1517 (1992). ERCC1 overexpression in gastric cancer patients has been reported to have a negative impact on tumor response and ultimate survival when treated with the chemotherapeutic regimen of cisplatin (DDP)/fluorouracil (Metzger, et al., J Clin Oncol 16: 309, 1998). Recent evidence indicates that gemcitabine (Gem) may modulate ERCC1 nucleotide excision repair (NER) activity. Thus, intratumoral levels of ERCC1 expression may be a major prognostic factor for determining whether or not DDP and GEM would be an effective therapeutic cancer patients.

Most pathological samples are routinely fixed and paraffin-embedded (FPE) to allow for histological analysis and subsequent archival storage. Thus, most biopsy tissue samples are not useful for analysis of gene expression because such studies require a high integrity of RNA so that an accurate measure of gene expression can be made. Currently, gene expression levels can be only qualitatively monitored in such fixed and embedded samples by using immunohistochemical staining to monitor protein expression levels.

Until now, quantitative gene expression studies including those of ERCC1 expression have been limited to reverse transcriptase polymerase chain reaction (RT-PCR) amplification of RNA from fresh or frozen tissue. U.S. Pat. No. 5,705,336 to Reed et al., discloses a method of quantifying ERCC1 mRNA from ovarian tumor tissue and determining whether that tissue will be sensitive to platinum-based chemotherapy. Reed et al., quanitfy ERCC1 mRNA from frozen ovarian tumor biopsies.

The use of frozen tissue by health care professionals as described in Reed et al., poses substantial inconveniences. Rapid biopsy delivery to avoid tissue and subsequent mRNA degradation is the primary concern when planning any RNA-based quantitative genetic marker assay. The health care professional performing the biopsy, must hastily deliver the tissue sample to a facility equipped to perform an RNA extraction protocol immediately upon tissue sample receipt. If no such facility is available, the clinician must promptly freeze the sample in order to prevent mRNA degradation. In order for the diagnostic facility to perform a useful RNA extraction protocol prior to tissue and RNA degradation, the tissue sample must remain frozen until it reaches the diagnostic facility, however far away that may be. Maintaining frozen tissue integrity during transport using specialized couriers equipped with liquid nitrogen and dry ice, comes only at a great expense.

Routine biopsies generally comprise a heterogenous mix of stromal and tumorous tissue. Unlike with fresh or frozen tissue, FPE biopsy tissue samples are readily microdissected and separated into stromal and tumor tissue and therefore, offer andvantage over the use of fresh or frozen tissue. However, isolation of RNA from fixed tissue, and especially fixed and paraffin embedded tissue, results in highly degraded RNA, which is generally not applicable to gene expression studies.

A number of techniques exist for the purification of RNA from biological samples, but none is reliable for isolation of RNA from FPE samples. For example, Chomczynski (U.S. Pat. No. 5,346,994) describes a method for purifying RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. Unfortunately, this method is not applicable to fixed and paraffin-embedded (FPE) tissue samples.

Other known techniques for isolating RNA typically utilize either guanidine salts or phenol extraction, as described for example in Sambrook, J. et al., (1989) at pp. 7.3–7.24, and in Ausubel, F. M. et al., (1994) at pp. 4.0.3–4.4.7. Again, none of the known methods provides reproducible quantitative results in the isolation of RNA from paraffin-embedded tissue samples.

Techniques for the isolation of RNA from paraffin-embedded tissues are thus particularly needed for the study of gene expression in tumor tissues, since expression levels of certain receptors or enzymes can be used to determine the likelihood of success of a particular treatment.

There is a need for a method of quantifying ERCC1 mRNA from paraffinized tissue in order to provide an early prognosis for proposed genotoxic cancer therapies. As a result, there has been a concerted yet unsuccessful effort in the art to obtain a quantification of ERCC1 expression in fixed and paraffinized (FPE) tissue. Accordingly, it is the object of the invention to provide a method for assessing ERCC1 levels in tissues fixed and paraffin-embedded (FPE) and prognosticate the probable resistance of a patient's tumor to treatment with DNA damaging agents, creating the type of lesions in DNA that are created by DNA platinating agents, by examination of the amount of ERCC1 mRNA in a patient's tumor cells and comparing it to a predetermined threshold expression level.

SUMMARY OF THE INVENTION

In one aspect of the invention there is provided a method for assessing levels of expression of ERCC1 mRNA obtained from fixed and paraffin-embedded (FPE) fixed and paraffin-embedded (FPE) tumor cells.

In another aspect of the invention there is provided a method of quantifying the amount of ERCC1 mRNA expression relative to an internal control from a fixed and paraffin-embedded (FPE) tissue sample. This method includes isolation of total mRNA from said sample and determining the quantity of ERCC1 mRNA relative to the quantity of an internal control gene's mRNA.

In an embodiment of this aspect of the invention, there are provided oligonucleotide primers having the sequence of ERCC1-504F (SEQ ID NO: 1) or ERCC1-574R (SEQ ID NO:2) and sequences substantially identical thereto. The invention also provides for oligonucleotide primers having a sequence that hybridizes to SEQ ID NO: 1 or SEQ ID NO:2 or their complements under stringent conditions.

In yet another aspect of the invention there is provided a method for determining a chemotherapeutic regimen for a patient, comprising isolating RNA from a fixed and paraffin-embedded (FPE) tumor sample; determining a gene expression level of ERCC1 in the sample; comparing the ERCC1 gene expression levels in the sample with a predetermined threshold level for the ERCC1 gene; and determining a chemotherapeutic regimen based on results of the comparison of the ERCC1 gene expression level with the predetermined threshold level.

DETAILED DESCRIPTION OF THE INVENTION

Figure 1:
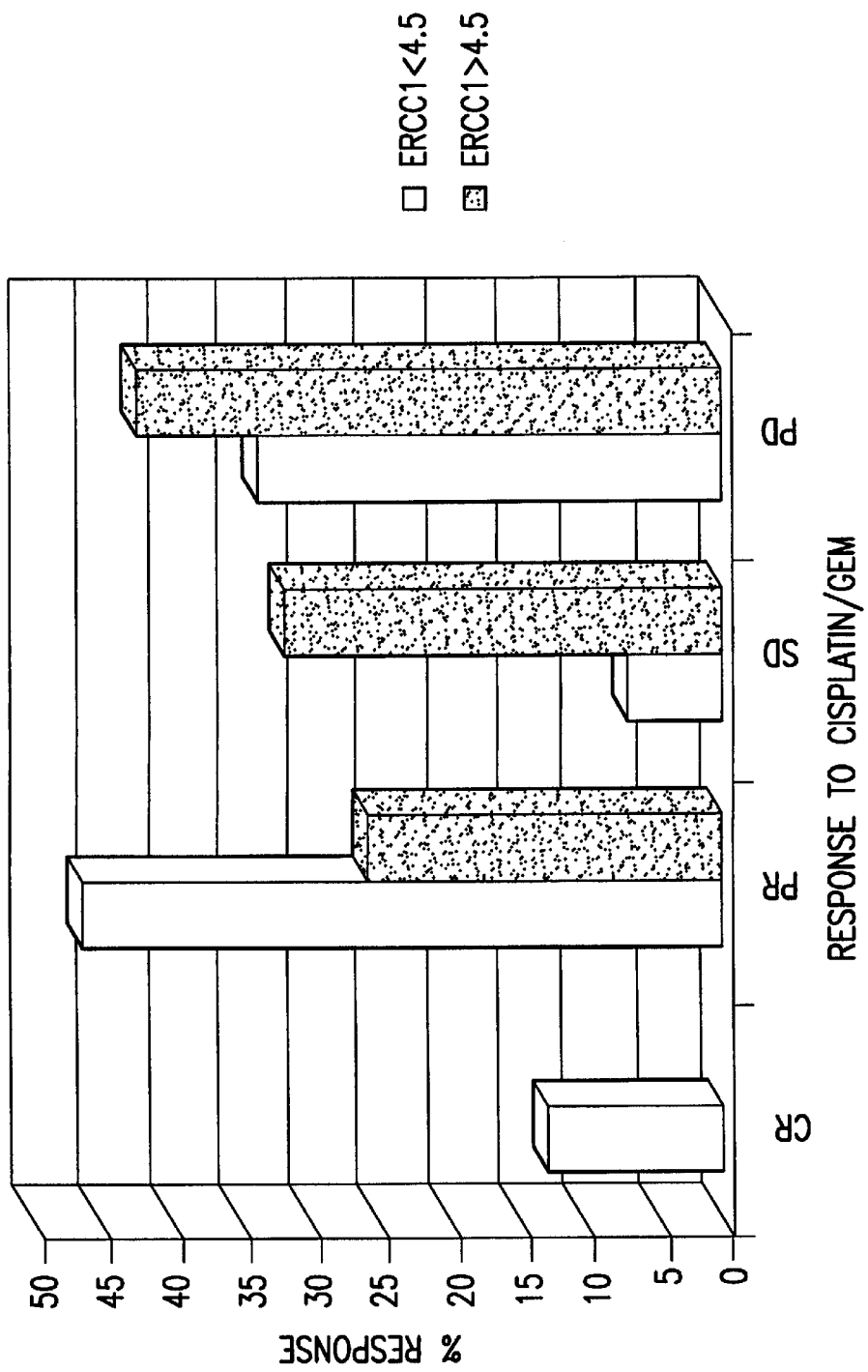
FIG. 1 is a graph showing the response of tumors to Cisplatin/Gem treatment vs. ERCC1 gene expression in NSCLC. Patients responding completely (CR) to Cisplatin/Gem treatment showed ERCC1 gene expression levels below the 4.5 threshold value, while most patients with progressive disease (PD) showed ERCC1 gene expression levels above 4.5. Partial response (PR), stable disease (SD).

The present invention resides in part in the finding that the amount of ERCC1 mRNA is correlated with resistance to DNA platinating agents. Tumors expressing high levels of ERCC1 mRNA are considered likely to be resistant to platinum-based chemotherapy. Conversely, those tumors expressing low amounts of ERCC1 mRNA are likely to be sensitive to platinum-based chemotherapy. A patient's relative expression of tumor ERCC1 mRNA is judged by comparing it to a predetermined threshold expression level.

The invention relates to a method of quantifying the amount of ERCC1 mRNA expression in fixed and paraffin-embedded (FPE) tissue relative to gene expression of an internal control. The present inventors have developed oligonucleotide primers that allow accurate assessment of ERCC1 expression in tissues that have been fixed and embedded. The invention oligonucleotide primers, ERCC1-504F (SEQ ID NO: 1), ERCC1-574R (SEQ ID NO: 2), or oligonucleotide primers substantially identical thereto, preferably are used together with RNA extracted from fixed and paraffin embedded (FPE) tumor samples. This measurement of ERCC1 gene expression may then be used for prognosis of platinum-based chemotherapy.

This embodiment of the invention involves first, a method for reliable extraction of RNA from an FPE sample and second, determination of the content of ERCC1 mRNA in the sample by using a pair of oligonucleotide primers, preferably oligionucleotide primer pair ERCC1-504F (SEQ ID NO: 1) and ERCC1-574R (SEQ ID NO: 2), or oligonucleotides substantially identical thereto, for carrying out reverse transcriptase polymerase chain reaction. RNA is extracted from the FPE cells by any of the methods for mRNA isolation from such samples as described in U.S. patent application Ser. No. 09/469,338, filed Dec. 20, 1999, and is hereby incorporated by reference in its entirety.

The present method can be applied to any type of tissue from a patient. For examination of resistance of tumor tissue, it is preferable to examine the tumor tissue. In a preferred embodiment, a portion of normal tissue from the patient from which the tumor is obtained, is also examined. Patients whose normal tissues are expected to be resistant to platinum-based chemotherapeutic compounds, i.e., show a high level of ERCC1 gene expression, but whose tumors are expected to be sensitive to such compounds, i.e. show a low level of ERCC1 gene expression, may then be treated with higher amounts of the chemotherapeutic composition.

The methods of the present invention can be applied over a wide range of tumor types. This allows for the preparation of individual "tumor expression profiles" whereby expression levels of ERCC1 are determined in individual patient samples and response to various chemotherapeutics is predicted. Preferably, the methods of the invention are applied to solid tumors, most preferably Non-Small Cell Lung Cancer (NSCLC) tumors. For application of some embodiments of the invention to particular tumor types, it is preferable to confirm the relationship of ERCC1 gene expression levels to clinical resistance by compiling a dataset that enables correlation of a particular ERCC1 expression and clinical resistance to platinum-based chemotherapy.

A "predetermined threshold level", as defined herein, is a level of ERCC1 expression above which it has been found that tumors are likely to be resistant to a platinum-based chemotherapeutic regimen. Expression levels below this threshold level are likely to be found in tumors sensitive to platinum-based chemotherapeutic regimen. The range of relative expression of ERCC1, expressed as a ratio of ERCC1: an internal control gene, among tumors responding to a platinum-based chemotherapeutic regimen is less than about 4.5. Tumors that do not respond to a platinum-based chemotherapeutic regimen have relative expression of ERCC1: an internal control gene ratio above about 4.5. FIG. 1.

In performing the method of this embodiment of the present invention, tumor cells are preferably isolated from the patient. Solid or lymphoid tumors or portions thereof are surgically resected from the patient or obtained by routine biopsy. RNA isolated from frozen or fresh samples is extracted from the cells by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of the RNA during the extraction process.

However, tissue obtained from the patient after biopsy is often fixed, usually by formalin (formaldehyde) or gluteraldehyde, for example, or by alcohol immersion. Fixed biological samples are often dehydrated and embedded in paraffin or other solid supports known to those of skill in the art. Non-embedded, fixed tissue may also be used in the present methods. Such solid supports are envisioned to be removable with organic solvents for example, allowing for subsequent rehydration of preserved tissue.

RNA is extracted from the FPE cells by any of the methods as described in U.S. patent application Ser. No. 09/469,338, filed Dec. 20, 1999, which is hereby incorporated by reference in its entirety. Fixed and paraffin-embedded (FPE) tissue samples as described herein refers to storable or archival tissue samples. RNA may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. RNA is then extracted from the sample.

For RNA extraction, the fixed or fixed and deparaffinized samples can be homogenized using mechanical, sonic or other means of homogenization. Rehydrated samples may be homogenized in a solution comprising a chaotropic agent, such as guanidinium thiocyanate (also sold as guanidinium isothiocyanate). Homogenized samples are heated to a temperature in the range of about 50 to about 100° C. in a chaotropic solution, which contains an effective amount of a chaotropic agent, such as a guanidinium compound. A preferred chaotropic agent is guanidinium thiocyanate.

An "effective concentration of chaotropic agent" is chosen such that at an RNA is purified from a paraffin-embedded sample in an amount of greater than about 10-fold that isolated in the absence of a chaotropic agent. Chaotropic agents include: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and β-mercaptoethanol (BME). The chaotropic solution may also contain RNAse inhibitors.

Homogenized samples may be heated to a temperature in the range of about 50 to about 100° C. in a chaotropic solution, which contains an effective amount of a chaotropic agent, such as a guanidinium compound. A preferred chaotropic agent is guanidinium thiocyanate.

RNA is then recovered from the solution by, for example, phenol chloroform extraction, ion exchange chromatography or size-exclusion chromatography. RNA may then be further purified using the techniques of extraction, electrophoresis, chromatography, precipitation or other suitable techniques.

The quantification of ERCC1 mRNA from purified total mRNA, which indicates the level of ERCC1 expression, can be determined from either fresh, frozen, fixed or fixed and paraffin-embedded (FPE) tissue samples by reverse-transcriptase polymerase chain reaction (RT-PCR) methods common in the art. For example, other methods of quantifying of ERCC1 mRNA include the use of molecular beacons and other fluorescently labeled probes useful in multiplex PCR. Additionally, the present invention envisages the quantification of ERCC1 mRNA via use of a PCR-free systems employing, for example fluorescent labeled probes similar to those of the Invader® Assay (Third Wave Technologies, Inc.). Most preferably, quantification of ERCC1 cDNA and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996;6:986–994) or Gibson et al., (Genome Res 1996;6:995–1001).

As used herein, a "house keeping" gene or "internal control" is meant to include any constitutively or globally expressed gene whose presence enables normalization of mRNA levels. Normalization is a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302–2306.

The methods of the invention are applicable to a wide range of tissue and tumor types and so can be used for assessment of clinical treatment of a patient and as a diagnostic or prognostic tool for a range of cancers including breast, head and neck, lung, esophageal, colorectal, and others. In a preferred embodiment, the present methods are applied to prognosis of Non-Small Cell Lung Cancer (NSCLC).

Pre-chemotherapy treatment tumor biopsies are usually available only as fixed paraffin embedded (FPE) tissues, generally containing only a very small amount of heterogeneous tissue. Such FPE samples are readily amenable to microdissection, so that ERCC1 gene expression may be determined in tumor tissue uncontaminated with stromal tissue. Additionally, comparisons can be made between stromal and tumor tissue within a biopsy tissue sample, since such samples often contain both types of tissues.

Generally, any oligonucleotide pairs that flank a region of ERCC1 gene may be to carry out the methods of the invention. Primers hybridizing under stringent conditions to a region of the ERCC1 gene for use in the present invention will amplify a product between 20–1000 base pairs, preferably 50–100 base pairs, most preferably less than 100 base pairs.

The invention provides specific oligonucleotide primers pairs and oligonucleotide primers substantially identical thereto, that allow particularly accurate assessment of ERCC1 expression in FPE tissues. Preferable are oligonucleotide primers, ERCC1-504F (SEQ ID NO: 1) and ERCC1 (SEQ ID NO: 2), (also referred to herein as the oligonucleotide primer pair ERCC1) and oligonucleotide primers substantially identical thereto. The oligonucleotide primers ERCC1-504F (SEQ ID NO: 1) and ERCC1, (SEQ ID NO: 2) have been shown to be particularly effective for measuring ERCC1 mRNA levels using RNA extracted from the FPE cells by any of the methods for mRNA isolation, for example as described Example 1 and in U.S. patent application Ser. No. 09/469,338, filed Dec. 20, 1999, which is hereby incorporated by reference in its entirety.

"Substantially identical" in the nucleic acid context as used herein, means hybridization to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Selective hybridization exists when the hybridization is more selective than total lack of specificity. See, Kanehisa, Nucleic Acids Res., 12:203–213 (1984).

This invention includes substantially identical oligonucleotides that hybridize under stringent conditions (as defined herein) to all or portion of the oligonucleotide primer sequence of ERCC1-504F (SEQ ID NO: 1), its complement or ERCC1-574R (SEQ ID NO: 2), or its complement.

Under stringent hybridization conditions, only highly complementary, i.e., substantially similar nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer ERCC1-504F (SEQ ID NO: 1), its complement or ERCC1-574R (SEQ ID NO: 2), or its complement.

Hybridization of the oligonucleotide primer to a nucleic acid sample under stringent conditions is defined below. Nucleic acid duplex or hybrid stability is expressed as a melting temperature ($T_m$), which is the temperture at which the probe dissociates from the target DNA. This melting temperature is used to define the required stringency conditions. If sequences are to be identified that are substantially identical to the probe, rather than identical, then it is useful to first establish the lowest temperature at which only holmologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5×Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

Oligonucleotide primers disclosed herein are capable of allowing accurate assessment of ERCC1 gene expression in a fixed or fixed and paraffin embedded tissue, as well as frozen or fresh tissue. This is despite the fact that RNA derived from FPE samples is more fragmented relative to that of fresh or frozen tissue. Thus, the methods of the invention are suitable for use in assaying ERCC1 expression levels in FPE tissue where previously there existed no way to assay ERCC1 gene expression using fixed tissues.

Genotoxic agents are those that form persistent genomic lesions and are preferred for use as chemotherapeutic agents in the clinical management of cancer. The rate of cellular repair of genotoxin-induced DNA damage, as well as the rate of cell growth via the cell division cycle, affects the outcome of genotoxin therapy. Unrepaired lesions in a cell's genome can impede DNA replication, impair the replication fidelity of newly synthesized DNA or hinder the expression of genes needed for cell survival. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions.

A general class of genotoxic compounds that are used for treating many cancers and that are effected by levels of ERCC1 expression are DNA alkylating agents and DNA intercalating agents. Psoralens are genotoxic compounds known to be useful in the photochemotherapeutic treatment of cutaneous diseases such as psoriasis, vitiligo, fungal infections and cutaneous T cell lymphoma. Harrison's Principles of Internal Medicine, Part 2 Cardinal Manifestations of Disease, Ch. 60 (12th ed. 1991). Another general class of genotoxic compounds, members of which can alkylate or intercalate into DNA, includes synthetically and naturally sourced antibiotics. Of particular interest herein are antineoplastic antibiotics, which include but are not limited to the following classes of compounds represented by: amsacrine; actinomycin A, C, D (alternatively known as dactinomycin) or F (alternatively KS4); azaserine; bleomycin; carminomycin (carubicin), daunomycin (daunorubicin), or 14-hydroxydaunomycin (adriamycin or doxorubicin); mitomycin A, B or C; mitoxantrone; plicamycin (mithramycin); and the like.

Still another general class of genotoxic agents that are commonly used and that alkylate DNA, are those that include the haloethylnitrosoureas, especially the chloroethylnitrosoureas. Representative members of this broad class include carmustine, chlorozotocin, fotemustine, lomustine, nimustine, ranimustine and streptozotocin. Haloethylnitrosourea first agents can be analogs or derivatives of any of the foregoing representative compounds.

Yet another general class of genotoxic agents, members of which alkylate DNA, includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, trofosfamide and the like. Oligonucleotides or analogs thereof that interact covalently or noncovalently with specific sequences in the genome of selected cells can also be used as genotoxic agents, if it is desired to select one or more predefined genomic targets as the locus of a genomic lesion.

Another class of agents, members of which alkylate DNA, include the ethylenimines and methylmelamines. These classes include altretamine (hexamethylmelamine), triethylenephosphoramide (TEPA), triethylenethiophosphoramide (ThioTEPA) and triethylenemelamine, for example.

Additional classes of DNA alkylating agents include the alkyl sulfonates, represented by busulfan; the azinidines, represented by benzodepa; and others, represented by, e.g., mitoguazone, mitoxantrone and procarbazine. Each of these classes includes analogs and derivatives of the respective representative compounds.

From the measurement of the amount of ERCC1 mRNA that is expressed in the tumor, the skilled practitioner can make a prognosis concerning clinical resistance of a tumor to a particular genotoxin, preferably a platinum-based chemotherapy, or to a chemotherapy inducing a similar type of DNA damage. Platinum-based chemotherapies cause a "bulky adduct" of the DNA, wherein the primary effect is to distort the three-dimensional conformation of the double helix. Such compounds are meant to be administered alone, or together with other chemotherapies such as gemcitabine (Gem).

Other platinum-based genotoxic chemotherapies can also include members of which form covalent DNA adducts, includes heavy metal coordination compounds, including platinum compounds. Generally, these heavy metal compounds bind covalently to DNA to form, in pertinent part, cis-1,2-intrastrand dinucleotide adducts. Generally, this class is represented by cis-diamminedichloroplatinum (II) (cisplatin), and includes cis-diammine-(1,1-cyclobutanedicarboxylato) platinum(II) (carboplatin), cis-diammino-(1,2-cyclohexyl) dichloroplatinum(II), and cis-(1,2-ethylenediammine) dichloroplatinum(II). Platinum first agents include analogs or derivatives of any of the foregoing representative compounds.

Tumors currently manageable by platinum coordination compounds include testicular, endometrial, cervical, gastric, squamous cell, adrenocortical and small cell lung carcinomas along with medulloblastomas and neuroblastomas. Trans-Diamminedichloroplatinum (II) (trans-DDP) is clinically useless owing, it is thought, to the rapid repair of its DNA adducts. The use of trans-DDP as a chemotherapeutic agent herein likely would provide a compound with low toxicity in nonselected cells, and high relative toxicity in selected cells. In a preferred embodiment, the platinum compound is cisplatin.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and hydration of sections:
(1) A portion of an approximately 10 NM section is placed in a 1.5 mL plastic centrifuge tube.
(2) 600 μL, of xylene are added and the mixture is shaken vigorously for about 10 minutes at room temperature (roughly 20 to 25° C.).
(3) The sample is centrifuged for about 7 minutes at room temperature at the maximum speed of the bench top centrifuge (about 10–20,000×g).
(4) Steps 2 and 3 are repeated until the majority of paraffin has been dissolved. Two or more times are normally required depending on the amount of paraffin included in the original sample portion.
(5) The xylene solution is removed by vigorously shaking with a lower alcohol, preferably with 100% ethanol (about 600 μL) for about 3 minutes.
(6) The tube is centrifuged for about 7 minutes as in step (3). The supernatant is decanted and discarded. The pellet becomes white.
(7) Steps 5 and 6 are repeated with successively more dilute ethanol solutions: first with about 95% ethanol, then with about 80% and finally with about 70% ethanol.
(8) The sample is centrifuged for 7 minutes at room temperature as in step (3). The supernatant is discarded and the pellet is allowed to dry at room temperature for about 5 minutes.

B. RNA Isolation with Phenol-Chloroform
(1) 400 μL guanidine isothiocyanate solution including 0.5% sarcosine and 8 μL dithiothreitol is added.
(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).
(3) The sample is then heated at about 95° C. for about 5–20 minutes. It is preferable to pierce the cap of the tube containing the sample with a fine gauge needle before heating to 95° C. Alternatively, the cap may be affixed with a plastic clamp or with laboratory film.
(4) The sample is then extracted with 50 μL 2M sodium acetate at pH 4.0 and 600 μL of phenol/chloroform/isoamyl alcohol (10:1.93:0.036), prepared fresh by mixing 18 mL phenol with 3.6 mL of a 1:49 isoamyl alcohol:chlorofonm solution. The solution is shaken vigorously for about 10 seconds then cooled on ice for about 15 minutes.
(5) The solution is centrifuged for about 7 minutes at maximum speed. The upper (aqueous) phase is transferred to a new tube.
(6) The RNA is precipitated with about 10 μL glycogen and with 400 μL isopropanol for 30 minutes at −20° C.
(7) The RNA is pelleted by centrifugation for about 7 minutes in a benchtop centrifuge at maximum speed; the supernatant is decanted and discarded; and the pellet washed with approximately 500 μL of about 70 to 75% ethanol.
(8) The sample is centrifuged again for 7 minutes at maximum speed. The upernatant is decanted and the pellet air dried. The pellet is then dissolved in an ppropriate buffer for further experiments (e.g., 50 pI. 5 mM Tris chloride, pH 8.0).

Example 2 mRNA Reverse Transcription and PCR

Reverse Transcription: RNA was isolated from microdissected or non-microdissected formalin fixed paraffin embedded (FPE) tissue as illustrated in Example 1 and as previously described in U.S. application Ser. No. 09/469,338 filed Dec. 20, 1999, which is hereby incorporated by reference in its entirety. After precipitation with ethanol and centrifugation, the RNA pellet was dissolved in 50 ul of 5 mM Tris/Cl at pH 8.0. M-MLV Reverse Transcriptase will extend an oligonucleotide primer hybridized to a single-stranded RNA or DNA template in the presence of deoxynucleotides, producing a complementary strand. The resulting RNA was reverse transcribed with random hexamers and M-MLV Reverse Transcriptase from Life Technologies. The reverse transcription was accomplished by mixing 25 μl of the RNA solution with 25.5 μl of "reverse transcription mix" (see below). The reaction was placed in a thermocycler for 8 min at 26° C. (for binding the random hexamers to RNA), 45 min at 42° C. (for the M-MLV reverse transcription enzymatic reaction) and 5 min at 95° C. (for heat inactivation of DNAse).

"Reverse transcription mix" consists of 10 ul 5×buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3mg/ml in 10 mM Tris-HCL, pH 7.5), 1.25 ul RNA Guard 24,800 U/ml (RNAse inhibitor) (Porcine #27-0816, Amersham Pharmacia) and 2.5 ul MMLV 200 U/ul (Life Tech Cat #28025-02).

Final concentrations of reaction components are: 50 mM Tris-HCl, pH 8.3, 75 mM KCl, 3 mM MgCl2, 1.0 mM dNTP, 1.0 mM DTT, 0.00375. mg/ml BSA, 0.62 U/ul RNA Guard and 10 U/ ul MMLV.

PCR Quantification of mRNA expression. Quantification of ERCC1 cDNA and an internal control or house keeping gene (e.g., β-actin) cDNA was done using a fluorescence based real-time detection method (ABI PRISM 7700 or 7900 Sequence Detection System [TaqMan®], Applied Biosystems, Foster City, Calif.) as described by Heid et al., (Genome Res 1996;6:986–994); Gibson et al., (Genome Res 1996;6:995–1001). In brief, this method uses a dual labelled fluorogenic TaqMan® oligonucleotide probe, (ERCC1-530Tc (SEQ ID NO: 3), $T_m$=70° C.), that anneals specifically within the forward and reverse primers. Laser stimulation within the capped wells containing the reaction mixture causes emission of a 3'quencher dye (TAMRA) until the probe is cleaved by the 5' to 3'nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflects the starting copy number of the sequence of interest. Comparison of the starting copy number of the sequence of interest with the starting copy number of the internal control gene provides a relative gene expression level. TaqMan® analyses yield values that are expressed as ratios between two absolute measurements (gene of interest/internal control gene).

The PCR reaction mixture consisted 0.5 μl of the reverse transcription reaction containing the cDNA prepared as described above 600 nM of each oligonucleoride primer (ERCC1-504F (SEQ ID NO:1), $T_m$=59° C. and ERCC1-574R (SEQ ID NO: 2), $T_m$=58° C.), 200 nM TaqMan® probe (SEQ ID NO:3), 5 U AmpliTaq Gold Polymerase, 200 μM each dATP, dCTP, dGTP, 400 μM dTTP, 5.5 mM $MgCl_2$, and 1×Taqman Buffer A containing a reference dye, to a final volume of less than or equal to 25 μl (all reagents Applied Biosystems, Foster City, Calif.). Cycling conditions were, 95° C. for 10 min, followed by 45 cycles at 95° C. for 15 s and 60° C. for 1 min.

The oligonucleotide primers ERCC1-504F (SEQ ID NO:1) and ERCC1-574R (SEQ ID NO: 2), used in the above described reaction will amplify a 71 bp product.

Example 3

ERCC1 Expression Correlates with Tumor Response

Response and survival are correlated with the level of ERCC1 expression in 56 patients with advanced non-small-cell lung cancer (NSCLC) treated with Gem 1200 mg/m² on days 1 and 8 plus DDP 100 mg/m² on day 1 every 3 weeks. Patient characteristics were: median age=59 years (range, 32–75 years); sex: 48 of the 56 patients were male (85.7%); PS=performance status (ECOG modification of Karnofsky traditional performance status scale: 0=fully active, able to carry on all predisease performance without restriction, 1=restricted in physically strenuous activity but ambulatory and able to carry out work of a light or sedentary nature): 48 patients (85.7%) were PS 0 or 1; weight loss: occurred in 21 patients; 40 patients (71% of the total number of patients) had Stage 4 distant metastatic disease. Median number of cycles: 3 (range 1–6).

Total mRNA was isolated from microdissected FPE pretreatment tumor samples, and relative mRNA expression levels of ERCC1:β-actin were measured using quantitative RT-PCR. A method for mRNA isolation from such samples is described in Example 1 and in U.S. patent application Ser. No. 09/469,338, filed Dec. 20, 1999, and is hereby incorporated by reference in its entirety. A reverse transcription/polymerase chain reaction (RT/PCR)-based assay system was used to determine the level of expression of ERCC1, and β-actin, as described in Example 2.

Using a threshold value of 4.5, 35/56 patients had high ERCC1 expression relative to internal control expression of gene β-actin. There were no differences in ERCC1 levels by gender, age, performance status, weight loss, stage, histology or number of cycles received. Overall response rate to the chemotherapeutic regimen was 46.7%. The response rate was significantly higher for 21 patients with low ERCC1 expression, i.e. <4.5 (57.9%) than for 35 patients with high ERCC1 expression, i.e. >4.5 (37%) (P=0.03). Overall median survival was 32.7 weeks (range, 24.8–40.6). These show that ERCC1 expression is a prognostic factor for response to DDP/Gem in advanced NSCLC.

What is claimed is:

1. An isolated and purified oligonucleotide primer of SEQ ID NO: 1 or an oligonucleotide at least or about 80% identical to SEQ ID NO: 1.

2. An isolated and purified oligonucleotide primer of SEQ ID NO: 2 or an oligonucleotide at least or about 80% identical to SEQ ID NO: 1.

3. A kit for detecting expression of an Excision Repair Cross-Complementing (ERCC1) gene comprising at least two oligonucleotide primers, said two oligonucleotide primers consisting of SEQ ID NO:1 or an oligonucleotide primer at least or about 80% identical to SEQ ID NO: 1 and SEQ ID NO: 2 or an oligonucleotide primer at least or about 80% identical to SEQ ID NO: 2.

* * * * *

UNITED STATES PATENT AND TRADEMARK OFFICE
CERTIFICATE OF CORRECTION

PATENT NO. : 6,518,416 B1 Page 1 of 1
APPLICATION NO. : 09/796491
DATED : February 11, 2003
INVENTOR(S) : Danenberg It is certified that error appears in the above-identified patent and that said Letters Patent is hereby corrected as shown below:

Column 14, line 58, change "1" to -- 2 --.

Signed and Sealed this

Twenty-second Day of January, 2008

JON W. DUDAS
*Director of the United States Patent and Trademark Office*

SEQUENCE LISTING

```
<160> NUMBER OF SEQ ID NOS:  3

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 1
gggaatttgg cgacgtaatt c                                              21

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 2
gcggaggctg aggaacag                                                  18

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 3
cacaggtgct ctggcccagc acata                                          25
```